United States Patent [19]

Shenkin et al.

[11] Patent Number: 5,451,525
[45] Date of Patent: Sep. 19, 1995

[54] METHOD AND MATERIALS FOR DETERMINING PARTICLE COUNT IN A FLOW CYTOMETER

[75] Inventors: Mark L. Shenkin, Pembroke Pines; Ronald M. Hamelik, Miami; James C. S. Wood, Coral Springs, all of Fla.

[73] Assignee: Coulter Corporation, Miami, Fla.

[21] Appl. No.: 836,638

[22] Filed: Feb. 14, 1992

[51] Int. Cl.$^6$ ............................................. G01N 33/48
[52] U.S. Cl. ....................................... 436/63; 436/164; 436/172; 436/536; 435/2; 435/7.24; 422/73
[58] Field of Search .................... 422/73, 82.05, 82.07; 436/63, 536, 164, 172; 435/2, 7.24

[56] References Cited

U.S. PATENT DOCUMENTS

| 4,331,862 | 5/1982 | Ryan | 235/92 PC |
|---|---|---|---|
| 4,499,052 | 2/1985 | Fulwyler | 422/73 |
| 4,661,913 | 4/1987 | Wu et al. | 436/63 |
| 4,704,891 | 11/1987 | Recktenwald et al. | 73/1 R |
| 4,751,179 | 6/1988 | Ledis et al. | 436/63 |
| 4,888,290 | 12/1989 | Kortright et al. | 435/240.27 |
| 4,989,978 | 2/1991 | Groner | 356/343 |
| 5,073,498 | 12/1991 | Schwartz et al. | 436/63 |

FOREIGN PATENT DOCUMENTS 470810  6/1991  European Pat. Off. .

OTHER PUBLICATIONS

"Poster" by Mercolino, et al., "An Unlysed Whole Blood Method for Determining Reproducible Absolute CD4+ Lymphocyte Counts by Flow Cytometry"; Seventh International Conference in AIDS, Florence, Italy, Jun. 19, 1991.

Flow Cytometry and Sorting, John Wiley & Sons Publishing; 353-358 (1979).

*Primary Examiner*—Steven Weinstein
*Assistant Examiner*—Lien Tran
*Attorney, Agent, or Firm*—Mitchell E. Alter

[57] ABSTRACT

A method is provided to ascertain the total number of cells per unit volume of a cell specimen in an apparatus which does not measure the volume of a suspension containing the specimen as it is being analyzed. The method includes mixing a suspension of a known quantity of particles having a first light scatter signal with a known volume of a cell specimen having a second light scatter signal different from the first light scatter signal to obtain a suspension having a concentration of particles per specimen volume, passing each of said particles and each cell in said cell specimen, in turn, through a light beam, each of said particles and cells producing at least one forward light scattering pattern, counting the number of cells and the number of particles in a portion of said suspension, and determining the total number of cells per unit volume of the specimen. In a preferred embodiment of the invention, the method further includes correlating the light scattering pattern and fluorescence signal of the particles to a predetermined ratio which represents a threshold of minimum instrument performance and adjusting, if the predetermined ratio has not been attained, the operation of said instrument, while the particles are within the incident beam of light, until the measured ratio reaches said predetermined ratio whereby the instrument is analyzing both particles and cells in said cell suspension.

18 Claims, No Drawings

METHOD AND MATERIALS FOR DETERMINING PARTICLE COUNT IN A FLOW CYTOMETER

FIELD OF THE INVENTION

This invention relates to a method for accurately determining the count per unit volume of particles suspended in a fluid containing two or more different particles. More particularly, the invention relates to determining the blood cell count per unit specimen volume of blood cells in a flow cytometric system wherein the flow cytometer does not measure the volume of a suspension containing the specimen as it is being analyzed and wherein the blood cells of interest are CD4 lymphocytes. In addition, this invention relates to the use of added particles as a quality control check during analysis of the specimen.

BACKGROUND AND PRIOR ART OF THE INVENTION

HTLV III or Human T-cell Leukemia Virus Type III, now commonly referred to as Human Immunodeficiency Virus ("HIV") is recognized to be the causative agent for human immunodeficiency syndrome or AIDS. The chronic nature of AIDS considered as approaching epidemic proportions in the United States and other countries is reflected by a surfeit of studies and efforts to develop diagnostic immunoassays for reliably and consistently detecting viral antigens and antibodies to such antigens in human peripheral blood. In substantial measure, monoclonal antibody technology has been recorded for developing such immunoassays.

HIV belongs to the retrovirus group of viruses. Retroviruses carry a positive-stranded RNA and a special enzyme called reverse transcriptase in its core which is used to convert viral RNA into DNA. This reverses the classical process of cellular transcription in which DNA is converted to RNA.

It is known that the HIV binds to CD4 lymphocytes because the protein on the surface of CD4 lymphocytes serves as a receptor or binding site for HIV [Dalgleish AG et al., Nature 312:763–767 (1985)]. HIV also can bind to and attack other cells, such as, monocytes, tissue macrophages, and cells in the brain, spinal cord and peripheral nerves. The life cycle of HIV calls for the virus entering the host patient through sexual activity or blood transfusion, for instance, and then binding to receptors on monocytes and lymphocytes. The virus penetrates the cell and sheds its envelope or protein coat so as to expose its viral RNA core. The reverse transcriptase converts the viral RNA core to DNA which is integrated into the host cell genome. New viral particles are produced in quantity until the membrane of the host cell is ruptured to release the new viral particles in the human blood system.

Diagnostic tests are commercially available at this time utilizing monoclonal antibodies to determine whether a person having the AIDS disease or has been immunologically exposed to the virus can be identified. Diagnosis of the disease is complicated by the fact that extended periods of incubation are required before symptoms of the disease are expressed. The highly infectious nature of the disease and the fact that its cure presently is not within scientific capability also increases the difficulty of investigating live virus and its adverse affect on the human immune system so that successful diagnostic tests can be developed.

Presently, absolute CD4 count is a generally accepted predictor of clinical HIV disease progression. Current methods for this measurement require multi-step sample preparation and are known to have cumulative errors related to determining both the proportion of CD4 lymphocytes and the absolute lymphocyte count. One method which attempted to solve this problem was presented in a "poster" at the Seventh International Conference on AIDS in Florence, Italy, Jun. 19, 1991. However, the disclosed method was incomplete since it did not teach nor enable one to practice the method.

Similarly, others have attempted to provide different methods and apparatuses to solve the general problem of determining the cell count per unit volume of particles suspended in a fluid containing undesirable particles. One approach is described in U.S. Pat. No. 4,989,978 to Groner. However, this method requires that a predetermined known volume of a suspension of cells and undesirable particles be analyzed so that the volume of the undesirable particles may be subtracted from the original predetermined volume to provide an accurate count of cells per unit volume.

More generally, others have added a plurality of particles to various diluents in methods for testing and calibrating flow cytometry instruments. Although the prior art contains many such disclosures, two such examples are U.S. Pat. No. 4,704,891 to Recktenwald, et al and U.S. Pat. No. 4,331,862 to Ryan. In addition, by adding standard particles to a cell suspension prior to analysis, a "built in" fiducial mark is provided which can be used to interrelate distributions obtained under differing instrument conditions. According to Flow Cytometry and Sorting, John Wiley & Sons Publisher, 1979, this built in technique is taught by Jensen, et al, Multiparameter Flow Cytometry Applied Toward Diagnosis of Cervical Squamous Cell Carcinoma. Proceedings of the Second International Conference on Automation of Cancer Cytology and Cell Image Analysis, May 6–7, 1977. However, these general references fail to address the problem of determination of cell count per specimen volume.

SUMMARY OF THE INVENTION

The present invention relates to a method for accurately determining the total number of cells per unit volume of a cell specimen in an apparatus which does not measure the volume of a suspension containing the specimen as it is being analyzed and which does not analyze the entire original known volume. The count of the cells is correlated to the count of the added discrete particles to determine the cell count per initial volume. In a preferred embodiment, the method employs a light scatter trigger to sense the cells, and uses a two scale analysis of light scatter and fluorescence to count the cells of interest and the added discrete particles, as well as, to discriminate between the cells of interest and added discrete particles. In a more preferred embodiment, the cells of interest are labelled with a fluorescent monoclonal antibody.

In one embodiment, the method of this invention comprises mixing a suspension of a known quantity of discrete particles with a known volume of the cell specimen to obtain a suspension having a concentration of particles per specimen volume; counting the number of cells and particles in a portion of said suspension; and determining the total number of cell per unit volume of the specimen. Said determination is obtained by correlating the ratio of said counted cells in said portion times the number of said known quantity of particles in the suspension to the specimen volume times the number of said counted particles in said portion.

In another embodiment, the method of this invention comprises mixing a suspension of a known quantity of particles having a first light scatter signal with a known volume of a cell specimen having a second light scatter signal different from the first light scatter signal to obtain a suspension having a concentration of particles per specimen volume; passing each of said particles and cells in said cell suspension, in turn, through a light beam, each of said particles and cells producing at least one forward light scattering pattern; counting the number of cells and the number of particles in a portion of said suspension; and, determining the total number of cells per unit volume of the specimen by correlating the number of particles and cells in said suspension to the known quantity of particles added to said cell specimen.

The use of this method permits the cell specimen to be subjected to one or more volumetric dilutions caused by the processing of the cells. More specifically, providing the original cell specimen volume is known, the cell specimen may be lysed, have cells of interest tagged with stain or monoclonal antibodies, or be subject to such other process which would dilute the original cell specimen volume to an unknown volume.

In addition, the invention further provides a quality control method to insure that the operating parameters of the counting instrument is within specification so that it accurately senses all of the desired particles, while simultaneously determining the count per unit volume of a cell suspension.

By using fluorescent particles with the cell specimen, the flow cytometer can use light scatter triggering for the parameter set so that the particles and cells are analyzed by light scatter and fluorescence. Providing that the cells and particles are sensed by light scatter and fluorescence during analysis, then one has adequate assurance that the flow cytometer has been properly operating during the analysis of the specimen.

In a preferred embodiment, the method of this invention further comprises the additional steps of correlating said light scattering pattern and fluorescence signal of the particles to a predetermined ratio which represents a threshold of minimum instrument performance and adjusting, if the predetermined ratio has not been attained, the operation of said instrument, while the particles are within the incident beam of light, until the measured ratio reaches said predetermined ratio whereby the instrument is analyzing both particles and cells in said cell suspension.

DETAILED DESCRIPTION OF THE INVENTION

In order to determine the total number of cells per unit volume of a cell specimen in an apparatus which does not measure the volume of a suspension containing the specimen as it is being analyzed, it is necessary to begin with a known volume of the specimen. The accuracy of determining the cell count per unit volume will depend, in part, upon the accuracy of the measurement of the specimen volume.

In order to expeditiously obtain the cell count of cells of interest per unit volume, it is preferred that the whole blood is lysed to remove the erythrocytes by such means as known to those skilled in the art. These means include hypotonic lysis, acid lysis, as well as, the use of magnetic particles or microspheres coated with an antibody for sorting and separating the selected population from a heterogeneous cell population. The only limiting fact in the selection of the method of lysis is that it should preserve the integrity of the leukocytes. More specifically, in a preferred embodiment of this invention, the preferred method of lysis of the whole blood is by the COULTER ® Immuno-Prep EPICS ™ Leukocyte Preparation System, distributed by Epics Division of Coulter Corporation (COULTER and EPICS are trademarks of Coulter Corporation, Hialeah, Fla.). As known to those skilled in the art, this preferred method of lysis is a hypotonic lysis.

Although the flow cytometer is capable of distinguishing between leukocytes of interest and erythrocytes in the whole blood, evaluation of a whole blood sample would require an extended time to analyze when using a light scatter trigger. The extended time is due to the cytometer having to analyze both the red blood cells as well as the white blood cells. More specifically, the white blood cell count in normal blood is 5,000 to 11,000 per microliter ($\mu L$) with a lymphocyte value of 20 to 40% and the red blood cells are 4,000,000 to 5,000,000 cells per microliter ($\mu L$). Therefore, in order to calculate a lymphocyte count of 5,000, approximately 10 million to 30 million cells will be analyzed.

After lysing the whole blood, the remaining leukocytes are then identified by such means as known to those skilled in the art. Such identification means includes stains, ligands, probes, and monoclonal antibodies. The selection of the stain, ligand, probe, or monoclonal antibody enables the enumeration of the selected leukocyte of interest to be identified and accurately counted in an expeditious manner.

Having determined the initial volume of the cell specimen, a known number of discrete particles are then added to the blood specimen which has optionally been lysed, and in which the labelled leukocytes of interest have been identified.

Both biological and plastic discrete particles known to those skilled in the art may be used in the present invention. The discrete particles should be inert with respect to the carrier in which they are diluted and with respect to the test probe of the counting instrument. In addition, the discrete particles should be stable at conventional working temperatures of 0°–30° C. Unstable particles have a tendency to shift in their histogram positioning, and contribute imprecision to the determination of cells per specimen volume. An important feature of the present invention is that the particles do not need to have characteristics of a like nature to the cells of interest. More specifically, the particles are not required to replicate the volume, size, fluorescence, light scatter, impedance, or Coulter opacity of the cells of interest. Using particles having different characteristics than the cells, eliminates any overlapping of cell count to cause erroneous or inaccurate results.

Preferably, the density of the discrete particle should approximate that of the cell. More specifically, the density of the particle should be greater than 1.0 grams per milliliter. This is advantageous because if the density is substantially disproportionate to the cells in the specimen, the discrete particles will have a tendency to settle in the specimen if not analyzed immediately. As such, if the discrete particles are substantially disproportionate to the density of the cells, a non-uniform mixture might be analyzed which could contribute to an inaccurate determination of cell count per unit volume. Therefore, if the density of the particle differs from the density of the cell specimen by greater than 20%, then the cell-particle suspension should be analyzed within 30 minutes of preparation. More preferably, the density of the particle should differ from the cells by less than 5%, and the cell-particle suspension should be analyzed within 4 hours of preparation.

The preferred type of particles for the present invention are plastic microbeads. Such beads may be fabricated with substantially uniform diameter, and have surface characteristics which are suitable for surface binding of fluorophores or other marking agents. Substantially spherical beads may be formed having a diameter between 0.5 and 20 microns. While the beads are usually made in solid form, they may be hollow inside and could be vesicles or other microcarriers. Moreover, the beads do not have to be perfect spheres in order to function in accordance with the present invention. Plastic materials such as polystyrene, polyacrylamide and other latex materials may be employed for fabricating the beads, and other plastic materials such as polyvinylchloride, polypropylene and the like may also be utilized.

When plastic particles are used, they should be treated to prevent the plastic particles from adhering to the cells in the cell-particle specimen and to prevent the plastic particles from aggregating with each other. These two impediments need to be resolved so that the particles remain discrete and are susceptible of accurate differentiation.

To prevent the plastic particles from adhering to the cells of interest, the particles may be coated with such substances which will counteract this tendency. Such substances include bovine serum albumin, glycolipid, polyvinylpyrrolidone or other substances which would change the bioreactivity of the plastic particle so that it would not attach to the cells of interest. For the purposes of this invention, it is preferred to use a bovine serum albumin solution.

It is believed that the aggregation of the plastic particles is caused by the surface charge of the discrete plastic particle. It has been found that this obstacle may be resolved by the aforementioned coating process. But in addition, the pH of the carrier appears to contribute to the resolution of the aggregation problem. Moreover, it is further believed that the use of a non-ionic surfactant would also contribute to eliminating this problem.

The carrier used as the storage and suspension medium for the particles must be chemically and physically compatible with the selected particle material and with the type of counting instrument. Thus, for use in those counting instruments which use the change in electrical conductivity to calculate count, the carrier must be electrically conductive. Those skilled in the art who use counting instruments employing the principle of electrical conductivity appreciate that the conductivity of the carrier will greatly affect the indicated count of the instruments. Thus, a standard carrier conductivity has been adopted and is the conductivity of 0.8% equivalent molarity of sodium chloride.

On the other hand, for those counting instruments which utilize the light scattering principle, the carrier must be optically conductive (or transparent, i.e., having a very low absorption coefficient). However, those skilled in the art who use counting instruments employing the principle of light scattering appreciate that when using certain plastic particles, such as DNA check beads, there is a tendency for them to aggregate. As noted previously, it is believed that the aggregation is caused by electrostatic attraction of the discrete plastic particles which may be related to the salt concentration in the carrier. Therefore, when using such particles in a light scattering instrument, the carrier should not cause aggregation of the plastic particles.

In a preferred embodiment of the invention, the carrier should have a density equal to or greater than the density of the added discrete particle. Preferably, the carrier density is between 0 to 15% and more preferably 0 to 5% greater than the discrete particle density. If the density of the carrier is substantially disproportionate to the discrete particle, then the particles will have a tendency to either settle to the bottom or float to the top of the carrier solution resulting in a non-homogeneous particle suspension. A homogeneous particle suspension is desirable to facilitate the procedure to add a known count of the particles to the cell specimen.

More preferably, the carrier comprises an aqueous solution of glycerol and most preferably comprises between 17 to 21% by volume of the aqueous solution. However, as known to those skilled in the art, other known media may be used to increase the carrier density, such as sucrose, Ficoll-Hypaqu TM (manufactured by Pharmacia L.K.B. Biotechnology), and Percoll TM (manufactured by Pharmacia L.K.B. Biotechnology). When DNA check beads are the particles of choice, the carrier will have a density within 5% difference of 1.03 grams/milliliter.

In order to maximize the life of the particles and carrier and to prevent further aggregation of the particles, it is important that the pH of the carrier be compatible with the particles and other additives in the carrier. For example, it has been found that a pH falling generally within the range of 6.0 to 8.0 is acceptable and that a preferable range is from 6.9 to 7.3 for use with particles of a latex material. If the pH of the carrier is either too high or too low, it has been found that the latex particles may aggregate, thereby diminishing the known total number of particles and further increasing the size of the aggregates to perhaps a size that would fall outside of the ability of the instrument to count the particles. It is noted that the term aggregation is used broadly and also includes the formation of doublets or triplets of particles which, it should be appreciated, would be as detrimental as the formation of much larger aggregates of particles.

In addition, it is also desirable to include in the carrier a small, but sufficient concentration of a preservative to prevent the growth of bacteria or fungi in the carrier or on the particles. More particularly, the preservative is preferably a fungicide and/or a bactericide which does not increase background noise by either creating floculations or adding fluorescence. Although any additive which is compatible with the other components of the carrier and with the particle material is acceptable, it is preferred that the preservative be selected from the group comprising organic aldehydes, including monaldehydes such as formaldehyde, or dialdehydes such as glutaraldehyde; alcohols, including organic alcohol, such as aliphatic and cylic alcohols, such as phenol, toluene, ethanol, and propanol; and sodium fluoride and sodium azide. More preferably, the additive selected is formaldehyde and is used in an amount within the range of about 0.5% to 2.5% and preferably 1.0% by volume of the carrier liquid.

It is believed that the stability of the carrier can be enhanced if an appropriate surfactant is added thereto. However, the selected surfactant must not deleteriously affect the cells of interest. Preferably, such a surfactant is non-ionic type and is present in the minimum amounts necessary so that the aggregation of particles is minimized. Too great a percentage of surfactant in the carrier results in the formation of bubbles, as well as, causes cell degradation, while too little surfactant does not provide the desired degree of stability.

For the purposes of this invention, the preferred procedure to add a known count of particles to the cell specimen comprises pipetting a selected volume of the carrier containing the discrete particles. The accuracy of determining the cell count per unit volume will depend, in part, upon the accuracy of the volumetric measurement of this particle suspension. By this method, the number of beads that can be added to the cell specimen is known within one percent. However, any method known to those skilled in the art to add a known count of particles to the cell specimen may be employed.

The unknown volume portion of the cell specimen and particles is analyzed by a method which is effective to determine the number of discrete particles and the number of cells of interest. Preferably, the method comprises light scatter triggering followed by light scatter and fluorescence measurements in a flow cytometer.

In typical flow cytometry instruments, cells and other discrete particles are caused to flow in a liquid stream so that each cell and particle, preferably one at a time, passes through a sensing region which measures one or more of its physical or chemical characteristics.

The sensing methods include electrical impedance related to particle volume based upon the well known Coulter Principle; fluorescence; light absorption; light scatter; light extinction; fluorescence polarization and fluorescence signal waveform. Any one or more of these sensing methods may be used to activate a particular parameter set of analysis.

For purposes of the ensuing discussion, and for exemplary purposes, reference is made to a flow cytometer wherein, the liquid flow stream of cells and particles is ensheathed in a sheath fluid so that the cells and particle stream may be hydrodynamically focused as it flows through an incident beam of light normally directed at right angles to the stream of cell and particle flow. As the cells and particles pass through the beam of light, light characteristics associated with each cell and particle triggers a particular parameter set of analysis which may optimally be selected by the instrument operator. Although fluorescence and light scatter are optical signals, when used as a trigger for a parameter set, each has a different function and effect.

When a light scatter trigger is employed, each cell and particle passing through the incident beam of light is sensed by junction silicon photodiodes. Since light scatter is affected by particle size, shape, density, stain uptake, and granularity, one or more of these criteria may be used to activate cell analysis. As such, cell analysis may be activated by requiring the cell and particle to meet an upper or lower threshold of these criteria.

When a fluorescence trigger is employed, only those cells and particles having a fluorescence is sensed by photomultiplier tubes which converts light signals to electrical signals. The fluorescent cells and particles absorb the incident beam offlight and emit a fluorescent signal at a light wavelength different from the incident source. Fluorescence is affected by the uniformity of illumination and signal intensity. Illumination uniformity is related to the stability of the light source and its spatial intensity distribution. Fluorescence signal intensity depends upon a variety of instrumental characteristics, included are the excitation light intensity, sample stream flow velocity, the illumination source and excitation spectra of the dye, quantum efficiency of the dye, collection and transmission efficiency of the light detection optics and the sensitivity of the photodetectors. As such, cell and particle analysis may be activated by requiring the particle to meet an upper or lower threshold of fluorescence signal intensity.

For the purposes of this invention, it is preferred that the method of sensing the particles comprises a light scatter trigger. This will enable all particles in the suspension to be analyzed by the parameter set selected. Moreover, a light scatter trigger is not dependent upon the signal intensity of a fluorescence stain which can vary on a cell by cell basis. More particularly, the use of a light scatter trigger will provide a two-fold benefit.

First, when the cells are analyzed, a light scatter trigger will provide the ability to differentiate among the three types of leukocytes in the cell specimen, and in addition, by the use of markers or tags, to detect selected cluster designation of lymphocytes.

Secondly, the use of a light scatter trigger enables an in situ quality control of the instrument performance. More specifically, the instrument will initially sense the cells and discrete particles by light scatter and depending upon their characteristics, will trigger a certain parameter set of measurements. Such parameter set will include the simultaneous measurement of the light scatter and one or more other sensing properties. This has the advantage that all particles would be detected which would provide an accurate representation of the particles and cells in the sample suspension.

In addition, a light scatter trigger has the further advantage that during the analysis of the sample suspension, the instrument operator can have assurance that the instruments operating within performance specifications and analyzing the sample suspension. More particularly, while the sample suspension is being analyzed, the technician can confirm, and if necessary adjust, the alignment of the instrument by its ability to detect and report in the proper position in the histogram the known discrete particles and the amplification of the signal intensity of the known discrete particles.

These parameters are not apparent during an analysis of a sample suspension which contains a limited number of cells of interest or which is of limited quantity or which contains contaminates which are detected by the instrument. In essence, the operator is able to validate the analysis by focusing upon the measurements during analysis to determine that the machine is properly functioning.

In a most preferred embodiment, the sample suspension is analyzed by a simultaneous measurement of light scatter and fluorescence to provide significantly more accurate sensing of the cells than the measurement of only light scatter or only fluorescence. Thus, when using fluorescent particles and fluorescent markers for CD4 lymphocytes in the cell suspension which has been lysed of red blood cells, quality control can be assured by triggering on light scatter of the discrete particles and the cells of interest and confirming detection with light scatter and fluorescence. Correlating these two signals enable assurance of uniformity of illumination, signal intensity and improvement in the discrimination between the cells of interest and discrete particles.

In the most preferred embodiment of this invention, the cell-particle suspension will be further analyzed to differentiate the three major populations of leukocytes, (i.e., lymphocytes, monocytes and granulocytes), as well as, determine the CD4 lymphocytes in a single assay. In this embodiment, fluorescence triggering is not merited because not all cells and particles of interest will have a fluorescence intensity susceptible to accurate and reproducible measurement.

The measurement of particles and cells occurs after the suspension has reached a steady state of flow. This will allow for hydrodynamic instabilities of the suspension flow to be eliminated. These instabilities are most apparent at the start and end of analysis when the particles and cells may either be tightly or loosely grouped together. Moreover, during steady state flow, the suspension is substantially free of air bubbles which has a tendency to impede measurements. When the frequency of particle distribution is nearly equal, a steady flow rate is achieved. This provides the most accurate interval for determining the cell count per unit volume resulting in an precision greater than 95%.

The features and advantages of the present invention are more fully shown with respect to the following non-limiting examples.

EXAMPLE 1

Preparation of Plastic Microspheres
Materials:
1. Plastic microspheres having a fluorescence intensity susceptible of measurement
2. Glycerol, ACS
3. Mannitol, ACS
4. Bovine Serum Albumin (BSA) (35% solution)
5. Formaldehyde (36%), ACS
6. Distilled, deionized water Procedure:
1. Suspend the plastic microspheres in 0.1% BSA+1% Mannitol in water and incubate with rocking for 60 minutes at ambient conditions.
2. Centrifuge the plastic microspheres in a swinging bucket centrifuge at 1000 RPM (200×G), 5 minutes, at ambient conditions.
3. Remove and discard the supernate.
4. Resuspend the plastic microspheres in 0.1% BSA+1% Mannitol in water and incubate with rocking for 60 minutes at ambient conditions.
5. Repeat steps 2, 3, and 4, except rock overnight.
6. Repeat steps 2 and 3.
7. Resuspend the plastic microspheres with 50 parts 0.1% BSA+1% Mannitol+1.0% Formaldehyde+20% Glycerol in water (bottling solution) to every one part plastic microspheres.
8. Transfer to a glass bottle and sonicate for 5 minutes.
9. Prepare serial dilutions in bottling solution such that 10,000 plastic microspheres (±100) is obtain in 100 $\mu$l.

EXAMPLE 2

Preparation and Analysis of Sample suspension for CD4 Lymphocyte Determination
1. 100 $\mu$l of whole blood specimen is added to a 12×75 mm polypropylene tube.
2. 10 $\mu$l of a CD4 monoclonal antibody reagent used to label the CD4 lymphocyte cells is added to the tube to form a suspension and said suspension is vortexed.
3. Incubation is continued for 10 minutes at ambient conditions.
4. The suspension is lysed to remove erythrocytes.
5. Add 100,000 plastic microspheres which have been treated as described in Example 1.
6. The sample is again vortexed to 50% of tube height.
7. Immediately before analysis, vortex again to 50% of tube height for 5 seconds.
8. The sample suspension is then analyzed by flow cytometric methods known to those skilled in the art in an EPICS® Profile Elite Flow Cytometer and the count of CD4 lymphocytes per unit specimen volume is obtained.

EXAMPLE 3

Preparation and Analysis of Sample Suspension for Cultured Leukemic Cells

The method of Example 2 is repeated except the whole blood is replaced with 100 $\mu$l of cultured leukemic cells and the CD4 monoclonal antibody reagent is replaced with a propidium iodine reagent.

After incubation for twenty minutes to allow iodine binding to non-viable cells, steps 4 through 8 of Example 2 are repeated. The results obtained are the number of viable cultured cells per unit specimen volume.

EXAMPLE 4

Preparation and Analysis of Sample Suspension for Reticulocytes

The method of Example 2 is repeated except instead of using 100 $\mu$l of whole blood, only 2 $\mu$l is used, and the CD4 reagent is replaced with a reticulocyte reagent, such as thiazole orange. After incubation for approximately 10 minutes, steps 5 through 8 of Example 2 are repeated. The results obtained are the number of reticulocytes per unit specimen volume.

While the invention has been described with reference to specific embodiments and compositions, it will be appreciated that numerous modifications, variations and embodiments are possible, as being within the spirit and scope of the invention.

We claim:
1. A method to ascertain a total number of cells per volume of a cell specimen in an apparatus which does not measure volume of a suspension containing the specimen as it is being analyzed, said method comprising the steps of:
 a. mixing a known quantity of particles with a known volume of a cell specimen to obtain a suspension having a concentration of particles per specimen volume, said particles remaining separate from the cells in said suspension,
 b. counting the number of cells and the number of particles in an unknown volume portion of said suspension by using a flow cytometer with a light scatter trigger, and
 c. determining the total number of cells per volume of the specimen by correlating the number of particles and cells in said unknown volume portion of the suspension to the known quantity of particles added to said cell specimen using light scatter measurements and fluorescent measurements.

2. The method of claim 1, wherein said particles have been treated to prevent them from attaching to the cells in the cell specimen.

3. The method of claim 1, wherein the cells in said cell specimen have been treated with an identifying reagent to differentiate a particular cell subpopulation.

4. The method of claim 3, wherein said particular cell subpopulation comprises CD4 lymphocyte cells.

5. The method of claim 1, wherein said cell specimen comprises whole blood.

6. The method of claim 5, which further comprises lysing the cell specimen to effectively eliminate the erythrocytes.

7. The method of claim 1, wherein said particles have fluorescence properties capable of instrumentation analysis.

8. The method of claim 7, wherein said particles comprise plastic microspheres.

9. The method of claim 8, wherein said plastic particles have a density less than 20% difference than the cells in the cell specimen.

10. The method of claim 1, wherein said counting of said cells and particles occurs after the cell specimen has reached a steady state of flow in the flow cytometer.

11. A method to ascertain a total number of cells per volume of a cell specimen in an apparatus which does not measure volume of a suspension containing the specimen as it is being analyzed, said method comprising the steps of:
   a. mixing a known quantity of particles having a first light scatter signal with a known volume of a cell specimen having a second light scatter signal different from the first light scatter signal to obtain a suspension having a concentration of particles per specimen volume,
   b. passing each of said particles and cells in an unknown volume portion of said cell suspension, in turn, through a light beam, each of said particles and cells pruducing at least one forward light scattering signal,
   c. counting the number of cells and the number of particles in said unknown volume portion of said suspension by using a flow cytometer with a light scatter trigger, and
   d. determining the total number of cells per volume of the specimen by correlating the number of particles and cells in said portion of the suspension to the known quantity of particles added to said cell specimen using light scatter measurements and fluorescent measurements.

12. The method of claim 11, wherein said particles are capable of emitting fluorescence at a plurality of known wavelengths.

13. The method of claim 12, which further comprises reporting said light scattering pattern and fluorescence signal in a histogram.

14. The method of claim 13, which further comprises (e) correlating said light scattering pattern and fluorescence signal of the particles to a predetermined ratio which represents a threshold of minimum instrument performance and (f) adjusting, if the predetermined ratio has not been attained, the operation of said instrument, while the particles are within the incident beam of light, until the measured ratio reaches said predetermined ratio whereby the instrument is analyzing both particles and cells in said cell suspension.

15. The method of claim 14, wherein said cells are labelled with one or more fluorescence agents to produce a fluorescence signal.

16. The method of claim 15, wherein said fluorescent reagent is used to tag CD-4 lymphocyte cells.

17. The method of claim 16, wherein said particles have been treated to prevent them from attaching to the cells in the cell specimen.

18. The method of claim 17, wherein said counting of said cells and particles occurs after the cell specimen has reached a steady state of flow in the flow cytometer.

* * * * *